United States Patent
Lee et al.

(10) Patent No.: US 9,658,093 B2
(45) Date of Patent: May 23, 2017

(54) MEASUREMENT DEVICE FOR WATER EXCHANGES ACROSS WATER/SEDIMENT INTERFACE

(71) Applicant: KOREA INSTITUTE OF GEOSCIENCE AND MINERAL RESOURCES, Daejeon (KR)

(72) Inventors: Bong Joo Lee, Daejeon (KR); Ji-Hoon Lee, Daejeon (KR); Heesung Yoon, Daejeon (KR); Eunhee Lee, Daejeon (KR)

(73) Assignee: Korea Institute of Geoscience and Mineral Resources, Daejeon (KR)

( * ) Notice: Subject to any disclaimer, the term of this patent is extended or adjusted under 35 U.S.C. 154(b) by 32 days.

(21) Appl. No.: 14/700,727

(22) Filed: Apr. 30, 2015

(65) Prior Publication Data
US 2015/0323363 A1 Nov. 12, 2015

(30) Foreign Application Priority Data
May 8, 2014 (KR) .......................... 10-2014-0055104

(51) Int. Cl.
G01F 1/34 (2006.01)
G01F 3/38 (2006.01)
G01N 15/08 (2006.01)
E21B 49/00 (2006.01)

(52) U.S. Cl.
CPC ................ G01F 3/38 (2013.01); E21B 49/00 (2013.01); G01N 15/08 (2013.01); G01N 15/0826 (2013.01)

(58) Field of Classification Search
CPC ..... G01F 1/20; G01F 3/36; G01F 3/38; G01F 7/00; G01N 33/246
USPC ....................................... 73/219, 223, 861.42
See application file for complete search history.

(56) References Cited

U.S. PATENT DOCUMENTS

| | | | |
|---|---|---|---|
| 2002/0095984 A1* | 7/2002 | Johnson | G01N 15/0826 73/152.05 |
| 2010/0198547 A1* | 8/2010 | Mulligan | E21B 41/0007 702/100 |
| 2013/0014570 A1* | 1/2013 | Lee | G01F 1/00 73/73 |

(Continued)

FOREIGN PATENT DOCUMENTS

GB 990591 * 4/1965

OTHER PUBLICATIONS

Kelly et al.; "Measuring the Hydraulic Conductivity of Shallow Submerged Sediments;" 2003.*

(Continued)

*Primary Examiner* — Benjamin Schmitt
(74) *Attorney, Agent, or Firm* — Rabin & Berdo, P.C.

(57) ABSTRACT

There is provided a water exchange meter being capable of automatically and continuously measuring the water exchange at the surface water/sediment interface in which a saturated vertical hydraulic conductivity of the sediment from the hydraulic head difference between a chamber and a storage pipe at a measurement location is measured, and after the measurement of the saturated vertical hydraulic conductivity, while the measurement device used in the measurement of the vertical hydraulic conductivity is maintained, a vertical hydraulic gradient between upper and lower portions of a chamber is continuously measured in situ.

3 Claims, 15 Drawing Sheets

(A)

(56) References Cited

U.S. PATENT DOCUMENTS

2014/0116114 A1* 5/2014 Lee ................ G01N 33/246
73/38

OTHER PUBLICATIONS

Belanger and Montgomery, "Seepage meter errors", Limnol. Oceanogr., 1992, pp. 1787-1795, vol. 37, No. 8.
W.C. Burnett et al., "Quantifying submarine groundwater discharge in the coastal zone via multiple methods", Science of the Total Environment, 2006, pp. 498-543, vol. 367, Issues 2-3.
O.W. Israelsen et al., "Canal lining experiments in the delta area, Utah", Utah Agr Exp Sta Tech Bull, 1944, 313, pp. 52.
D.R. Lee, "A device for measuring seepage flux in lakes and estuaries", Limnology and Oceanography, Jan. 1977, pp. 140-147, vol. 22, No. 1.
Ann E. Mulligan et al., "Intercomparison of submarine groundwater discharge estimates from a sandy unconfined aquifer", Journal of Hydrology, 2006, pp. 411-425, vol. 327.
Ronald J. Paulsen et al., "Development and Evaluation of an Ultrasonic Ground Water Seepage Meter", Ground Water, Nov.-Dec. 2001, pp. 904-911, vol. 39, No. 6.
Edward Sholkovitz et al., "An automated dye-dilution based seepage meter for the time-series measurement of submarine groundwater discharge", Limnology and Oceanography: Methods 1, 2003, pp. 16-28.
Makoto Taniguchi et al., "Continuous Measurements of Ground-Water Seepage Using an Automatic Seepage Meter", Ground Water, Jul.-Aug. 1993, pp. 675-679, vol. 31, No. 4.
Makoto Taniguchi et al., "Measurements of submarine groundwater discharge rates by a continuous heat-type automated seepage meter in Osaka Bay, Japan", J Groundw Hydrol, 2001, pp. 271-277, vol. 43.

* cited by examiner (schematic diagram of saturation report conductivity measuring device)

(A)

(In-situ testing location)

(time points of measurement of a vertical hydraulic conductivity in relation to variance in tidal height)

(K (a, b, c) at time points of measurement, and K (d) by using the entire measurement values)

(head variance measured at upper port of the chamber)

(head variance measured at lower port of the chamber)

(vertical hydraulic gradient variance measured at upper and lower ports of the chamber)

(Darcian flux variance at the surface water/sediment interface measured at one location of Bangdu Bay of Jeju Island)

(water exchange variance at the surface water/sediment interface measured at one measurement location of Bangdu Bay of Jeju Island)

MEASUREMENT DEVICE FOR WATER EXCHANGES ACROSS WATER/SEDIMENT INTERFACE

TECHNICAL FIELD

The present invention relates to a measuring device of water exchange at surface water/sediment interface by measuring a vertical hydraulic conductivity (K) and a vertical hydraulic gradient (i) in relation to the sediment beneath the surface water/sediment interface. More particularly, the present invention relates to a water exchange meter at surface water/sediment interface, which is given by laying a cylindrical chamber, open at its bottom but closed at its top, into the sediment beneath the surface water/sediment interface, and being capable of automatically and continuously measuring the water exchange at the surface water/sediment interface by measuring a saturated vertical hydraulic conductivity of the sediment inside the chamber, and while maintaining the chamber, by measuring a vertical hydraulic gradient between two different level elevations of the chamber.

BACKGROUND ART

Surface water and ground-water interaction is very active and mutually communicated with each other, while physical and chemical changes in either one influence to the other one. Thus, surface water and groundwater have been recognized as one interplaying resource. Surface water and groundwater interaction is the subject essentially required to research and verify in many aspects such as analysis of hydrological balance, finding of transfer paths of nutrients and contaminants, research and development of groundwater movement systems, securing and planning of water resources, and so on. Surface water and groundwater interaction includes the discharge of water from aquifer (water bearing layer) to surface water layer or recharge of water from surface water layer to water bearing layer. It is desperately required to develop the methods and the means of directly or indirectly measuring the water exchange amount at the surface water/sediment interface in order to quantitatively analyze the discharge and the recharge of water at the surface water/sediment interface.

Until now, various methods have been proposed and employed in order to directly or indirectly measure the mutual interaction and water exchange amount of surface water and groundwater, for example, the method based on modeling, natural tracer, seepage meter, and temperature profiling, or the method of calculating the water exchange by measuring a vertical hydraulic gradient and a vertical hydraulic conductivity (Burnett et al., 2006). Among them, the seepage meter which is normally applied for water exchange measuring means in the search field except for natural tracer, and Darcian flux calculation of measuring water exchange amount by using a vertical hydraulic gradient and a vertical hydraulic conductivity (Mulligan and Charette, 2006) are mostly used. The seepage meter was used in 1940s and 1950s in order to measure water loss amount in irrigation ditches (Israelson and Reeve, 1944), and Lee (1977) designed a half-barrel seepage meter and used for the interaction research and evaluation of groundwater and stream water. As the efforts to solve and overcome the problems and disadvantages raised in the seepage meter by Lee (1977), there have been proposed seepage meters enabled to continuously and automatically measure the water exchange by using various methods, such as Heat pulse (Taniguchi and Fukuo, 1993), Continuous heat pulse (Taniguchi and Iwakawa, 2001), Ultrasonic (Paulsen et al., 2001), Dye-dilution (Sholkovitz et al., 2003), and so on. However, the automatic seepage meters as above are not commercialized yet, and thus, many researchers still use the seepage meter by the method of Lee (1977) for now, but the problem due to low reliability in the measured values by the Lee type seepage meter is still remained (Belanger and Montgomery, 1992).

The Darcian flux calculation as above is the method of calculating Darcian flux (q) from a vertical hydraulic conductivity of the sediment at the surface water interface and a vertical hydraulic gradient. The correctness and preciseness of the measurement results by the Darcian flux depends on the reliability of the values of the vertical hydraulic conductivity and the vertical hydraulic gradient. However, errors occurred when the measurement locations of the vertical hydraulic conductivity and the vertical hydraulic gradient are varied are still raised as problems to be solved.

Therefore, research and development of the means for measuring water exchange at the surface water/sediment interface by the Darcian flux calculation method in order to solve the above problems has been desperately required.

DISCLOSURE

Technical Problem

Therefore, the present invention has been made to solve the above problems, and it is an aspect of the present invention to provide a device for automatically and continuously measuring the water exchange at the surface water/sediment interface by measuring a saturated vertical hydraulic conductivity of the medium at the location to be measured, and then while a chamber used for measurement is maintained, continuously measuring a vertical hydraulic gradient between two points, upper and lower portions inside the chamber in the state of nature.

Other objects and advantages of the invention will become apparent from embodiments of the invention to be described later. The objects and advantages of the invention can be embodied by means described in the appended claims and combinations thereof.

Technical Solution

In accordance with the present invention, the above and other aspects can be accomplished by measuring the vertical hydraulic conductivity of the sediment filled inside the chamber 10 by using the permeameter for in-situ measurements of saturated hydraulic conductivity (registration No. 10-1366057) by the inventor of the present invention and then, by disconnecting a connection line 40 connecting a storage pipe 25 and the chamber 10 so that one end of the connection line 40 to the chamber 10 is open and placed inside water to freely come in and out, or by opening the top and bottom end of the chamber 10 so that the water through the sediment filling the chamber 10 is freely flowed in the vertical direction, and then by installing a vertical hydraulic gradient measuring unit 50 detachably and respectively at both sides to the chamber 10 and to communicate with the chamber 10 via the upper and lower portions of the chamber 10, so as to continuously measure a vertical hydraulic gradient between upper and lower portions of the chamber 10 distanced apart from each other.

The Darcy's law which is used in the present invention is a phenomenologically derived equation which describes the flow of a fluid through a porous medium such as sand layer, and is formulated based on the results that the water in the porous medium flows from higher hydraulic head to lower hydraulic head, and the flow of the water through the porous medium is proportional to a vertical hydraulic conductivity and a vertical hydraulic gradient (Equation 1). The Equation 1 describes Darcian flux (q), which is the discharge per area and per time of fluid at the surface water/sediment interface, derived by achieving the vertical hydraulic gradient (i) based on experiments, and then, multiplying a vertical hydraulic conductivity (K) to the vertical hydraulic gradient (i). Therefore, the water exchange at the surface water/sediment interface is calculated by multiplying the cross-section area (A) of a chamber 10 and the measured times (t) to the Darcian flux (q).

$$q = -Ki \quad \text{Equation (1)}$$

Advantageous Effects

As described above, in accordance with the present invention, the water exchange at the surface water/sediment interface can be automatically and continuously measured by which a saturated vertical hydraulic conductivity of the sediment where the measurement takes place is measured and then, while the meter of the present invention is maintained, a vertical hydraulic gradient between two different level upper and lower elevations inside the chamber is continuously measured.

DESCRIPTION OF DRAWINGS

These and other aspects and advantages of the present invention will become apparent and more readily appreciated from the following description of the embodiments, taken in conjunction with the accompanying drawings, in which.

Figure 1:
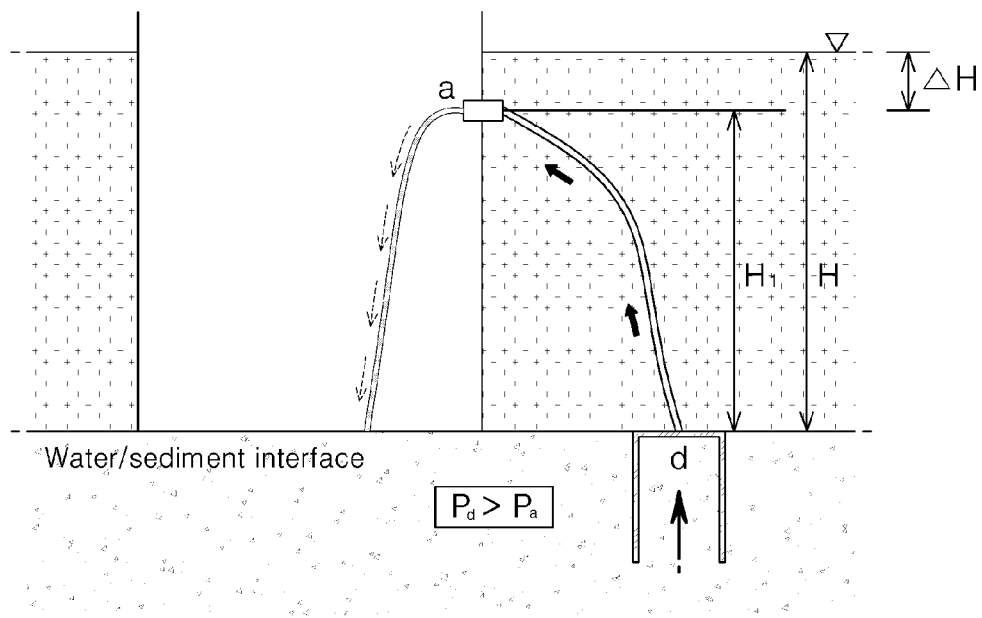
FIG. 1 is a schematic view conceptually showing the measurement of a saturated vertical hydraulic conductivity by using the hydraulic head difference between a storage pipe 25 and a chamber 10 according to the present invention.

[Brief description of reference numbers of major elements]

| | |
|---|---|
| 10: chamber | 11: connection line |
| 12: level bar | 20: measuring unit of vertical hydraulic conductivity |
| 21: first hydraulic head measurement line | |
| 22: second hydraulic head measurement line | |
| 23: manometer | 24: hand vacuum pump |
| 25: storage pipe | 26: insertion part |
| 27: inlet | 28: pressing part |
| 29: pressure means | 30: first automatic water level measurer |
| 40: connection line | 50: vertical hydraulic gradient measuring unit |
| 51: first pipe | 52: second pipe |
| 53: communicater | 54a, 55b: second automatic level measurers |

Best Mode

The present invention to achieve the above aspects has the characteristics as follows:

In accordance with an embodiment of the present invention, there is a water exchange meter at surface water/sediment interface comprising: a chamber fixedly installed at the bottom of stream and filling medium there inside; a measuring unit of vertical hydraulic conductivity including a storage pipe to communicate with the chamber by a connection line and to have a hydraulic head difference with the chamber for measuring the hydraulic head difference between upper and lower portions inside the chamber, and measuring the amount of the water induced into the storage pipe from the lower portion to the upper portion inside the chamber and measuring the flow rate of the water so as to obtain a saturated vertical hydraulic conductivity of the medium; and a vertical hydraulic gradient measuring unit installed around and at both of the chamber to enable to detach from the chamber after the saturated vertical hydraulic conductivity is measured and the measuring unit of vertical hydraulic conductivity is removed from the chamber, and communicatedly connected to the chamber through upper and lower portions of the chamber for continuously measuring the vertical hydraulic gradient between two portions of the upper and lower of the chamber and by multiplying the vertical hydraulic gradient and the saturated vertical hydraulic conductivity so as to measure the water exchange through the chamber.

Mode for Invention

The present invention will now be described more fully hereinafter with reference to the accompanying drawings, in which preferred embodiments of the invention are shown.

It will be understood that words or terms used in the specification and claims shall not be interpreted as the meaning defined in commonly used dictionaries. It will be further understood that the words or terms should be interpreted as having a meaning that is consistent with their meaning in the context of the relevant art and the technical idea of the invention, based on the principle that an inventor may properly define the meaning of the words or terms to best explain the invention.

As used herein, the singular forms "a", "an" and "the" are intended to include the plural forms as well, unless the context clearly indicates otherwise.

The present invention may be embodied in different forms and should not be construed as limited to the embodiments set forth herein. Rather, these embodiments are provided as teaching examples of the invention. Therefore, it will be understood that the scope of the invention is intended to include various modifications and alternative arrangements within the capabilities of persons skilled in the art using presently known or future technologies and equivalents.

FIG. 1 is a view conceptually showing the measurement of a saturated vertical hydraulic conductivity according to the present invention, and a chamber is inserted into a stream bed deposit and an empty barrel is provided in the stream bed and a tube is installed between the chamber and the barrel. The height of the inlet of the empty barrel which is connected to the chamber by the tube, is located as low as ΔH lower than the water surface. When ignoring the interaction of surface water and sediment such as gain stream or loss stream, the hydraulic head (Pd) inside the chamber 10 is ρgH equal to the height of the water surface. The hydraulic head (Pa) of the connect point of the tube with the empty barrel is ρgH1. The hydraulic head of the chamber is higher as long as ρgΔH than the hydraulic head of tube connect point at the inlet of the barrel. The groundwater of saturation zone is moving upwardly by the hydraulic head difference through the chamber so as to finally gather in the empty barrel. As ΔH is increased, the hydraulic head difference is increased so that water flow passing through the chamber is increased. At this time, the vertical hydraulic conductivity of the sediment inside the chamber is calculated by the ratio of the hydraulic head difference between the two points inside the chamber and the water flow discharged into the empty barrel.

Figure 2:
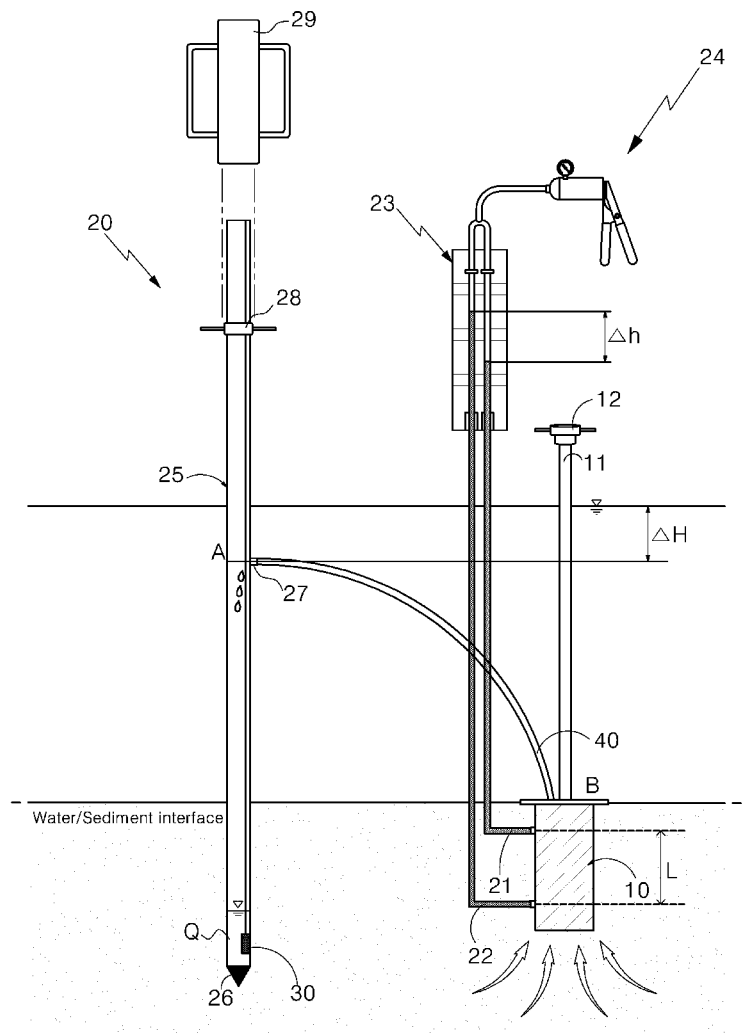
FIG. 2 is a schematic view conceptually showing the configuration of the meter for measuring a vertical hydraulic conductivity according to one embodiment of the present invention (permeameter for in-situ measurements of saturated hydraulic conductivity; registration No. 10-1366057)
Figure 3:
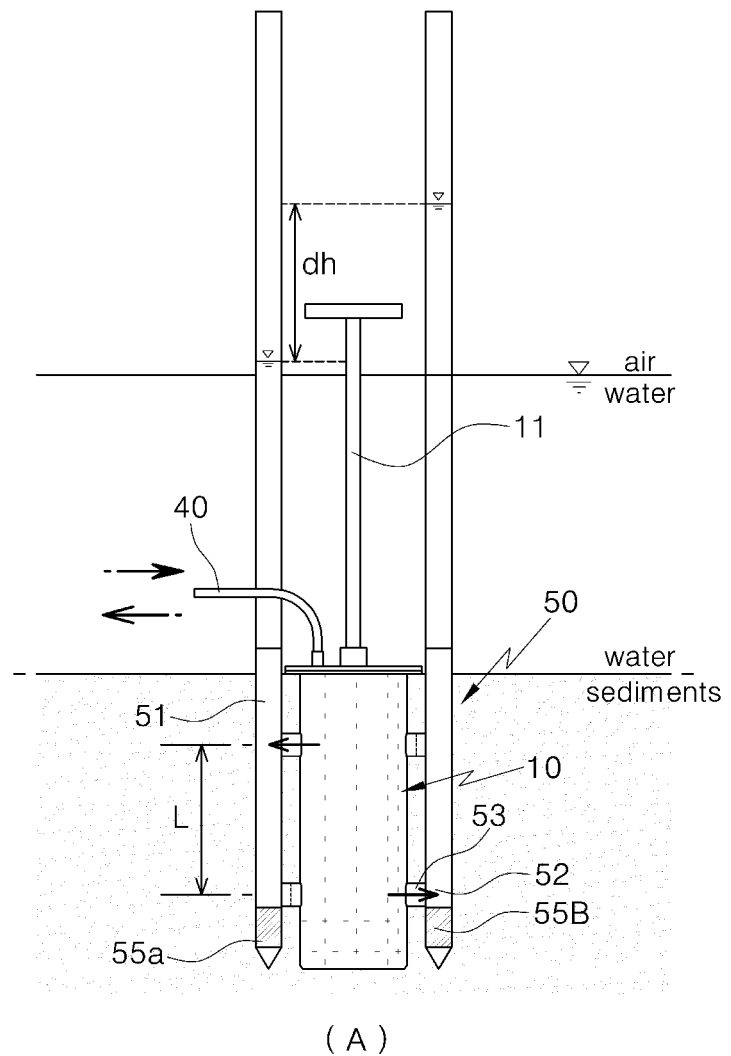
FIG. 3 is a schematic view conceptually showing the configuration of the meter for measuring a vertical hydraulic gradient inside a chamber according to one embodiment of the present invention.
Figure 4:
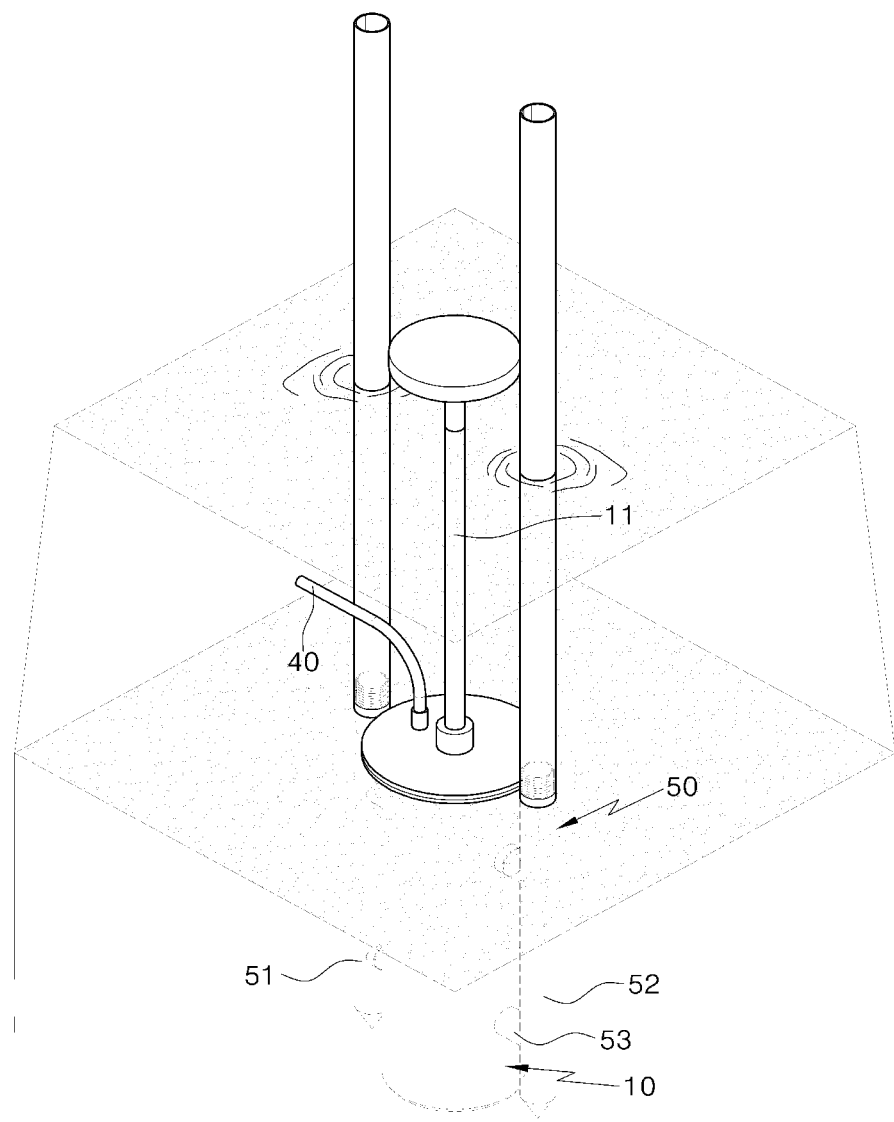
FIG. 4 is a perspective view of FIG. 3.
Figure 5:
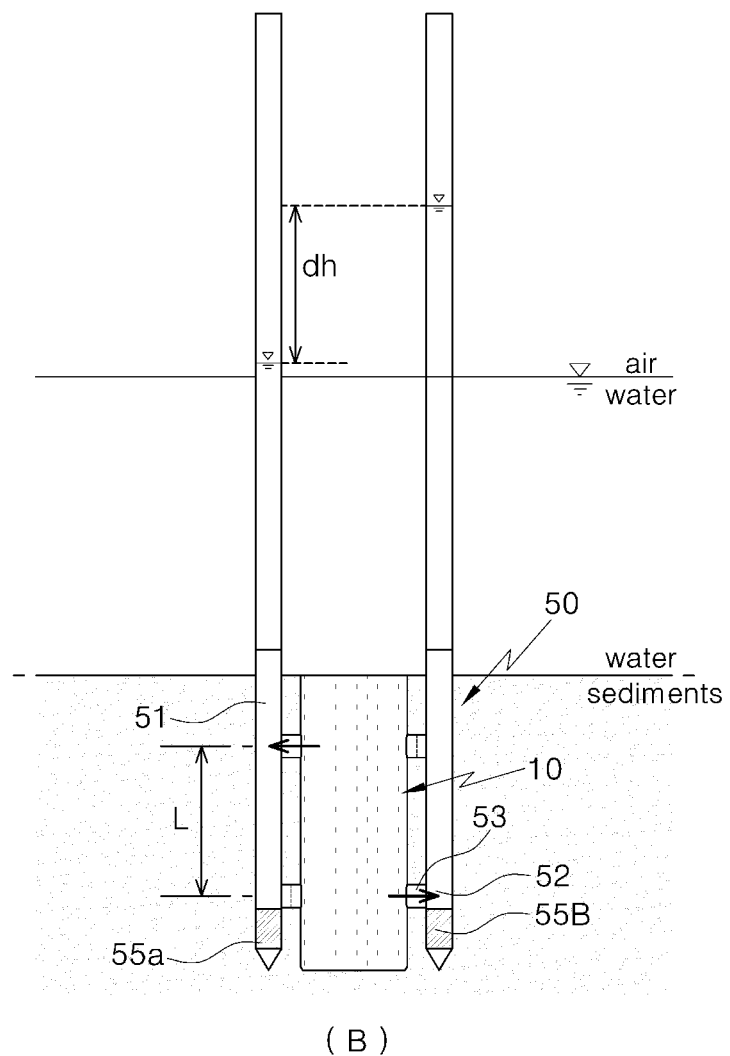
FIG. 5 is a schematic view showing the configuration of the meter for measuring a vertical hydraulic gradient with the top of the chamber 10 being open according to one embodiment of the present invention.
Figure 6:
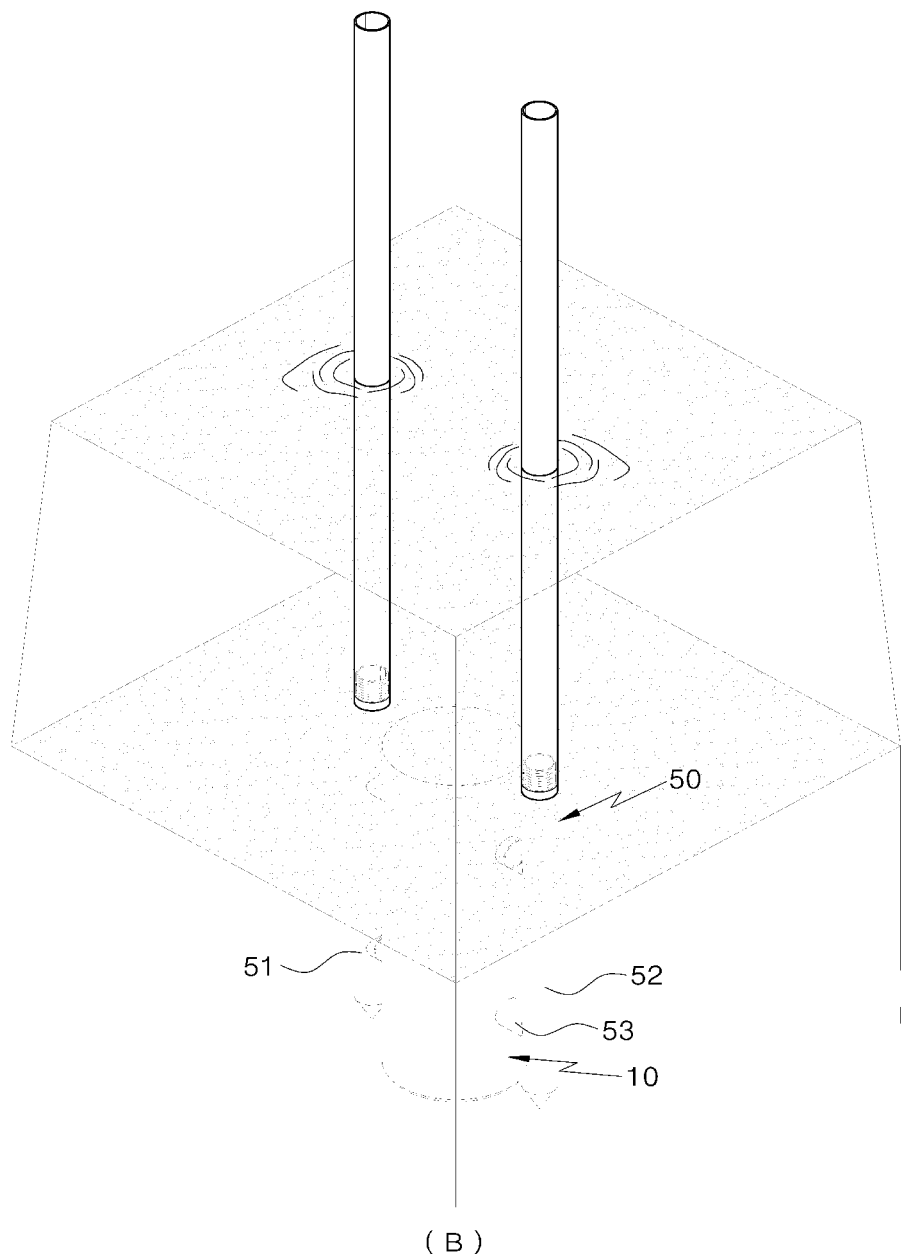
FIG. 6 is a perspective view of FIG. 5.
Figure 7:
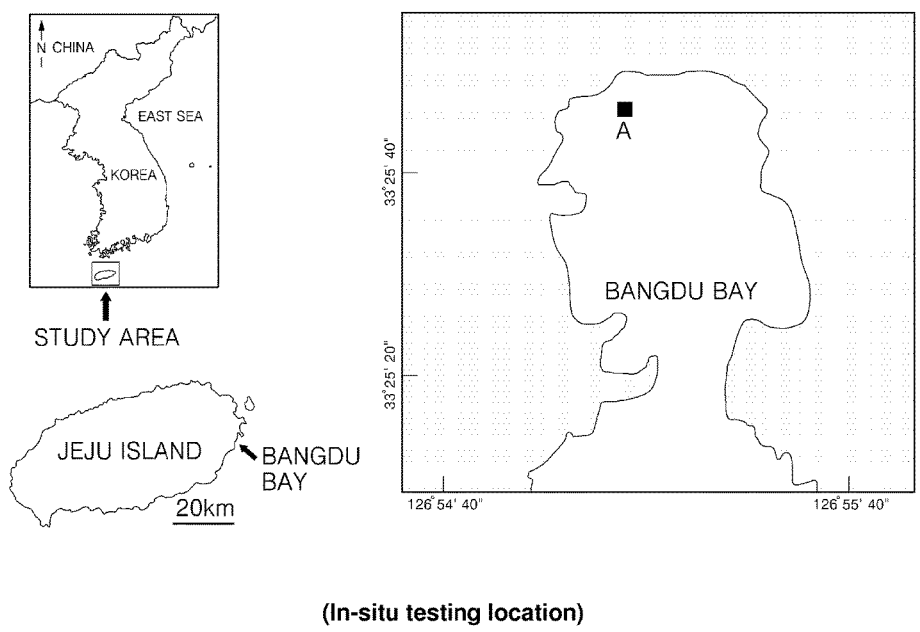
FIG. 7 is a view of showing in-situ testing location.

As shown in FIG. 2 illustrating one embodiment of the meter for measuring the saturated vertical hydraulic conductivity by a chamber 10 and a measuring unit of vertical hydraulic conductivity 20 according to the present invention, the chamber 10 and a storage pipe 25 are installed with distanced apart from each other and their ends put into the bottom of stream, and rise perpendicularly out of water and sediment interface, and the chamber 10 and the storage pipe 25 are connected to each other by a connection line 40. As the chamber 10 is embedded, the top end of the chamber 10 should be slowly pressed for the sediment not to be disturbed. The placing depth of the storage pipe 25 is determined so that an inlet 27 is placed lower than the water surface. As the storage pipe 25 is embedded into the sediment to rise perpendicularly so that the inlet 27 of the storage pipe 25 is placed lower than the water surface, the hydraulic head difference between the inlet 27 and the chamber 10 is generated, and due to this hydraulic head difference (ΔH), water is flowed from the chamber 10 to the inlet 27 of the storage pipe 25. The groundwater around the chamber 10 is induced into the chamber 10 so as to cause the water flow from the lower portion to the upper portion of the chamber 10 and incur the hydraulic head difference (ΔH) between the lower portion and the upper portion of the chamber 10. As the placing depth of the inlet 27 of the storage pipe 25 under the water surface is fixed, the water flow passing through the chamber 10 and the hydraulic head difference (ΔH) between the lower and the upper portion of the chamber 10 are constant. Thus, the ratio of these values of the measurement is calculated which is vertical hydraulic conductivity (the vertical hydraulic conductivity in Darcy's law is ratio of Darcian flux to hydraulic gradient.)

Hereinafter, referring to FIGS. 2 to 15, the measurement of the saturated vertical hydraulic conductivity by using the meter of measuring water exchange at the surface water/sediment interface according to one embodiment of the present invention will be described in detail.

As illustrated in FIG. 2 showing the water exchange Darcian flux meter at the surface water/sediment interface according to one embodiment of the present invention, the saturated vertical hydraulic conductivity (K) of the sand sediment by using the chamber 10 and the measuring unit of vertical hydraulic conductivity 20, can be measured by measuring the water exchange discharged according to the vertical hydraulic gradient artificially induced, and by analyzing the relation of the vertical hydraulic gradient and Darcian flux. The water exchange Darcian flux meter includes the chamber 10, the first and second hydraulic head measurement lines 21 and 22, the connection line 40, and the storage pipe 25.

The chamber 10 is a cylindrical shape with empty there inside and its bottom open, and is perpendicularly embedded upright into the sediment at the surface water/sediment interface by slowly pressing the top end of the chamber 10. The chamber 10 is filled with the sediment of saturation zone, such as sand through the open bottom end. An extension line 11 is provided on the top end of the chamber 10 to be extended out of the water surface, and a level bar 12 is provided at the top end of the extension line 11 to be perpendicular to the extension line 11 so that it is determined whether the chamber 10 is perpendicularly embedded into the water surface/sediment interface through the level state of the level bar 12. The level bar 12 is also used as handle when installing or removing the chamber 10. A cover detachably placed at the top of the chamber 10 can be removed and then, the vertical hydraulic gradient can be measured with the top end and the bottom end of the chamber 10 are open. At this case, the extension line 11 and the level bar 12 of the extension line 11 can be also removed.

The first and second hydraulic head measurement lines 21 and 22 are provided such that their respective one ends are connected at the upper and lower outer circumferences of the chamber 10 and the other ends are placed to protrude out of the surface water. The first hydraulic head measurement line 21 is connected to the upper circumference of the chamber 10 and the second hydraulic head measurement line 22 is connected to the lower circumference of the chamber 10 (relatively lower than the position of the first hydraulic head measurement line 21). The first and second hydraulic head measurement lines 21 and 22 are provided to measure the hydraulic head difference (Δh) due to the hydraulic head loss at the two different points in the chamber 10 as the water inside the chamber 10 is flowed from the lower portion to the upper portion of the chamber 10 (ex: manometer 23 and hand vacuum pump 24). The ends of the first and second hydraulic head measurement lines 21 and 22, which are connected to the chamber 10, are provided with mesh in order to prevent the sediment inside the chamber 10 induced into the lines 21 and 22.

The connection line 40 is made of a flexible tube, and its one end is connected to the top of the chamber 10 to be communicated with each other, and the other end of the connection line 40 is connected to the inlet 27 at the outer circumference of the storage pipe 25 to be communicated with each other. Thus, the water passing through the chamber 10 is induced into the inlet 27 of the storage pipe 25 through the connection line 40, (a nozel is installed at the inlet 27 to be communicated with the connection line 40) so as to fill the storage pipe 25.

The storage pipe 25 is a long and hollow tube, and has a circular shape in its cross section. The top end of the storage pipe 25 is open, and the other end thereof is pointed to form an insertion part 26 so that the storage pipe 25 can be firmly driven into the sediment. The storage pipe 25 is fixed to stand upright with a predetermined distance away from the chamber 10. The storage pipe 25 is fixed to the bottom of stream by pushing the sharp end of the insertion part 26 of the storage pipe 25 into the bottom of the stream. The open top end of the storage pipe 25 is directed upwardly to the opposite and the upper portion of the storage pipe 25 is out of the top surface of the stream upto a predetermined length so that the water of the stream is not inflowed into the storage pipe 25 through the top end of the storage pipe 25. The depth of the storage pipe 25 under the surface of the stream 25 is controlled by hitting a pressing part 28 which is protruded outwardly from the circumference of the storage pipe 25 by using a pressure means 29, a slide hammer.

The storage pipe 25 is a cylindrical pipe of constant cross section, and it may be determined whether the amount of water and inflow rate of water are constant by detecting the change of the level of water induced into the storage pipe 25. When the inflow rate of water induced into the storage pipe 25 is constant, the level of the water inside the storage pipe 25 is increased linearly. Therefore, Darcian flux can be calculated by selecting the linear block in which the water level is changed, and from the time period for the selected block, the total amount of inflow water, and the cross section area of the chamber 10. The level change of the water inside the storage pipe 25 can be measured by using a first automatic water level measurer 30 which is located at the bottom inside the storage pipe 25. Darcian flux and the hydraulic head difference ($\Delta h$) between the upper and lower portions inside the chamber 10 yields saturated vertical hydraulic conductivity of the sediment by the formula (1).

The inlet 27 is placed on the outer circumference of the storage pipe 25, and the other end of the connection line 40 described above is connected to the inlet 27 to communicate with each other. The hydraulic head difference ($\Delta H$) between the storage pipe 25 and the chamber 10 can be controlled by varying the location of the inlet 27 of the storage pipe 25, that is, the location of the other end of the connection line 40 to communicate to the storage pipe 25. The lower the inlet 27 to which the connection line 40 is connected to becomes inside water stream (the inlet 27 is directed to the other end of the storage pipe 25), the hydraulic head difference ($\Delta H$) between the storage pipe 25 and the chamber 10 is increased, and so, the amount of water Q which is induced into the storage pipe 25 is also increased. With variance of the location of the inlet 27 of the storage pipe 25 by intervals, Darcian flux in each interval which is induced and stored from the chamber 10 into the storage pipe 25, and the hydraulic head difference ($\Delta h$) between the upper and lower portions of the chamber 10 are measured, so as to calculate saturated vertical hydraulic conductivity of the sediments to be concerned in each interval. As the vertical hydraulic conductivity of the porous medium inside the chamber 10 to be measured is unique constant in each medium, and if the vertical hydraulic conductivity in each interval is correctly measured, the values of vertical hydraulic conductivity in all intervals must be same so that the vertical hydraulic gradient in each interval and Darcian flux must show a linear function relation. That is, it is possible to verify the accuracy of the vertical hydraulic conductivity obtained by the meter of the present invention by either way of simply comparing the vertical hydraulic conductivity in each interval, or seeing whether vertical hydraulic gradient in each interval and Darcian flux must show a linear function relation, or by determining whether the straight line leaning of the linear function of the relation is equal to the vertical hydraulic conductivity pre-known or not.

The inner diameter of the chamber 10 installed to stand straight on the sediment is 13.4 cm, the length of the chamber 10 is 40.0 cm, and the clearance between the first and the second hydraulic head measuring lines 21, 22 connected to the chamber 10 is 20.0 cm, and the first and the second hydraulic head measuring lines 21, 22 are respectively distanced with 10.0 cm from the upper and lower portions of the chamber 10.

After measuring the saturated vertical hydraulic conductivity as described above, now it will be described below one embodiment of the present invention in order to measure the water exchange at the surface water/sediment interface by continuously measuring the hydraulic head difference between the two portions of the chamber 10 (upper and lower portions) in the water exchange meter at the surface water/sediment interface according to the present invention.

As shown in FIGS. 3 to 6, in the structure of the measuring unit of vertical hydraulic conductivity 20 which was used to measure the saturated vertical hydraulic conductivity as described, the first and second hydraulic head measuring lines 21 and 22 and the storage pipe 25 are separated, and a vertical hydraulic gradient measuring unit 50 is connected in order to measure the vertical hydraulic gradient between the upper and lower portions, two points inside the chamber 10. The vertical hydraulic gradient measuring unit 50 includes first and second pipes 51 and 52, and second automatic level measurers 55a and 55b.

When the storage pipe 25 is disconnected, the connection line 40 one end of which was connected to the storage pipe 25 is placed inside water, its one end being open inside water, the connection line 40 should be placed with distanced apart from the sediment with a predetermined length, so that the sediment is not to be induced into the chamber 10 through the connection line 40.

The first and second pipes 51 and 52 are pipes having circular shape in cross section, its one bottom end being closed and its top end being open. The first and second pipes 51 and 52 are placed to stand right in face to each other with the chamber 10 placed between them. The first pipe 51 is placed in the left side of the outer circumference of the chamber 10, the upper portion of which is communicated with the first pipe 51. The second pipe 52 is placed in the right side of the outer circumference of the chamber 10, the lower portion of which is communicated with the second pipe 52.

The lower portions of the first and second pipes 51 and 52 are gradually sharp-pointed so that the first and second pipes 51 and 52 and the chamber 10 are easily put into the sediment, and the upper portions of the first and second pipes 51 and 52 are exposed out of water with a predetermined length (the length of the first and second pipes 51 and 52 can be variously employed in advance by considering the changes of surface level of water).

The automatic level measurers are installed inside the lowest of the first and second pipes 51 and 52 respectively at the same height so as to automatically and continuously measure the hydraulic head difference between the two portions of the chamber 10 (upper and lower portions respectively communicating with the first and second pipes 51 and 52).

By hydraulic head difference (Δh) obtained from the two hydraulic heads of the chamber 10 which are communicated with the first and second pipes 51 and 52, and the vertical distance (L) between the two portions, the vertical hydraulic gradient between two portions can be achieved.

Thus, the water exchange through the chamber 10 can be achieved by multiplying the vertical hydraulic gradient value by the saturated vertical hydraulic conductivity value of the sediment inside the chamber 10.

The experiment and measurement of the water exchange at the surface water/sediment interface by using the water exchange meter at surface water/sediment interface according to the present invention was performed at the Bangdu Bay (Hwang, 2002) located at the east of Jeju Island where the vertical flow of water at the surface water/sediment interface is clearly seen and the tide at the surface of the sea is highly fluctuating.

The first and second pipes 51 and 52, each pipe being 3 m in length, are installed to stand right on both sides of the chamber 10, and distanced with a predetermined length apart from the chamber 10, which is inserted perpendicularly into the interface sediment (40 cm in length and 13.4 cm in diameter). The first and second pipes 51 and 52 are connected respectively to the chamber 10 to communicate with by two ports, at upper and lower portions of the chamber 10, and include the automatic level measurers 55a and 55b respectively at their lower sides there inside.

Figure 8:
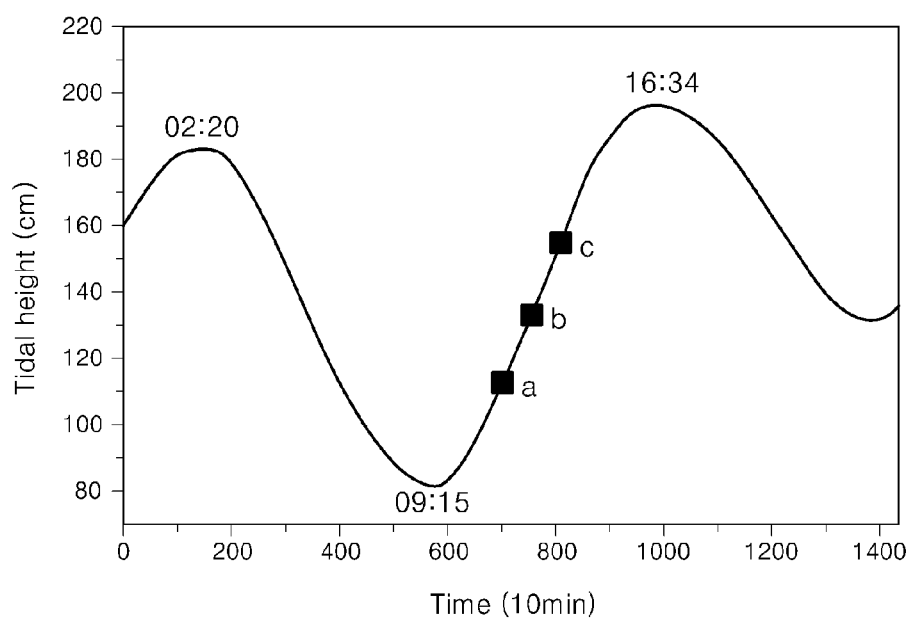
FIG. 8 is a view showing the time points of measurement of a vertical hydraulic conductivity in relation to variance in tidal height.

As illustrated in FIG. 8, a vertical hydraulic conductivity of the sand sediment filled inside the chamber 10 was measured by three times during the time when the tidal height changed from low to high before the hydraulic head difference inside the chamber 10 was measured.

Figure 9:
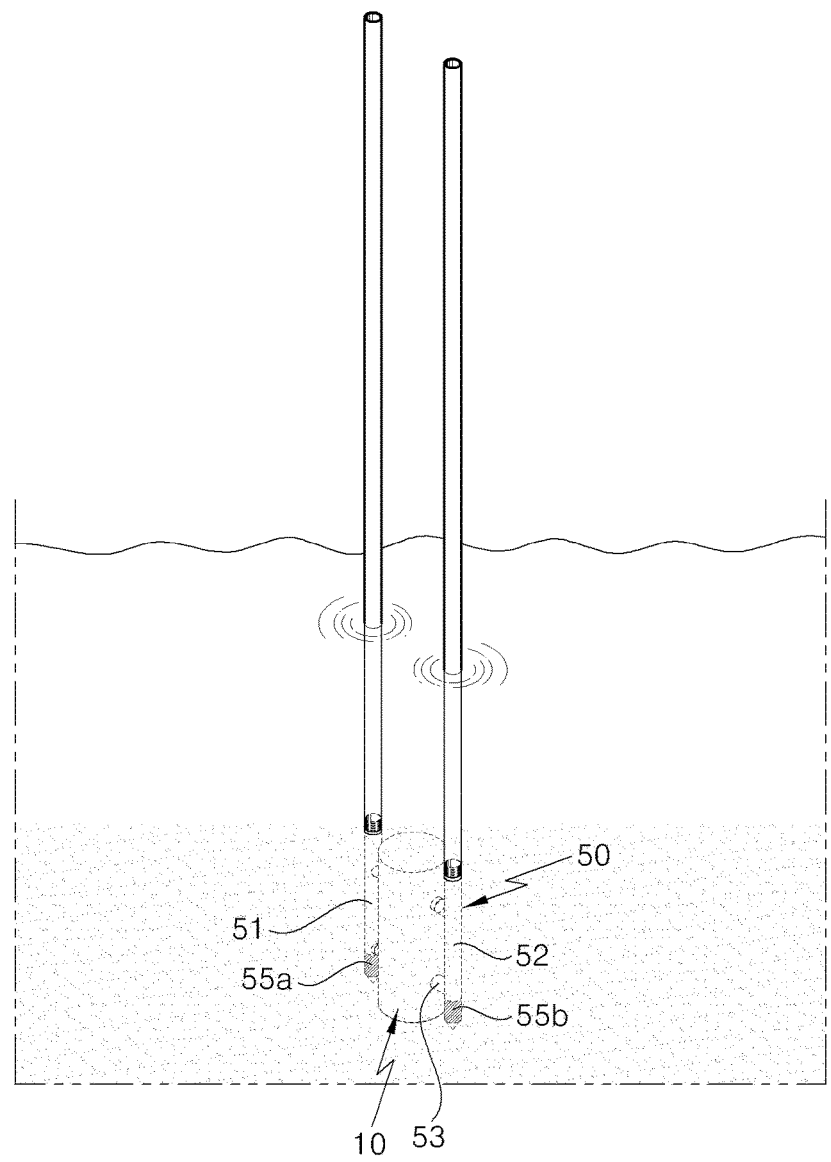
FIG. 9 is an in-situ testing photograph showing the meter according to the present invention.

FIG. 9 shows an in-situ testing photograph where the water exchange was being measured by using the water exchange meter at the surface water/sediment interface according to the present invention. The first and second pipes 51 and 52 vertically standing as shown in the center of the photograph are a kind of a manometer for measuring the hydraulic head of two points of the chamber 10 which are distanced away from. The automatic level measurers 55a and 55b are respectively installed in the bottom of the first and second pipes 51 and 52 so as to measure the hydraulic head variance at each measurement location.

Figure 10:
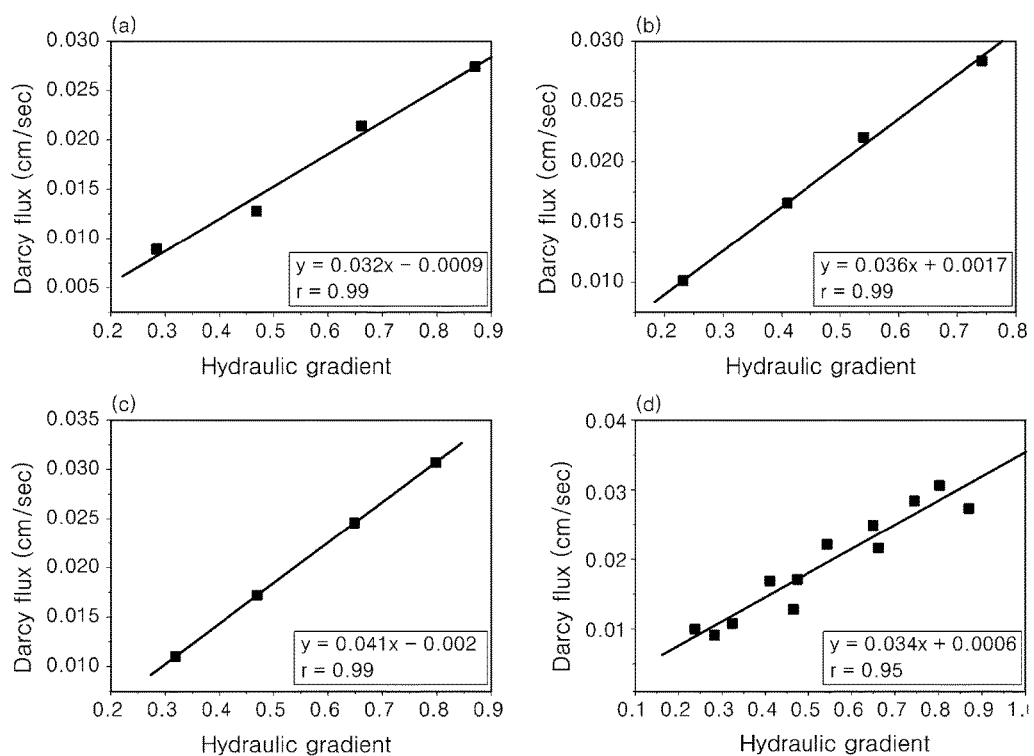
FIG. 10 is a view of the graphs showing the values of the vertical hydraulic conductivity (a, b, c) at time points of measurement, and the vertical hydraulic conductivity (d) by using the entire measurement values.

As shown in FIG. 10, the vertical hydraulic conductivity of the sand sediment inside the chamber 10 measured by three times are 0.032, 0.036, and 0.041 cm/sec, which are almost the same and thus indicate that the measurement values of the vertical hydraulic conductivity are highly correct because the correlation coefficient between the vertical hydraulic gradient and Darcian flux is 0.99 or higher. The vertical hydraulic conductivity obtained by using the measurement values of the vertical hydraulic gradient and Darcian flux is 0.034 cm/sec. The saturated vertical hydraulic conductivity in the calculation of the water exchange in the embodiment of the present invention is 0.034 cm/sec.

Figure 11:
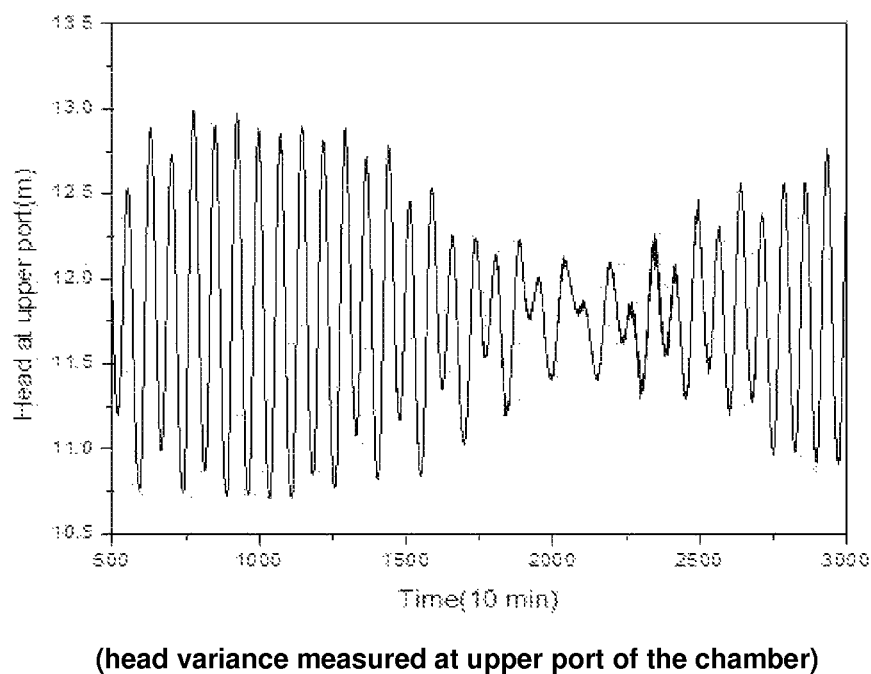
FIG. 11 is a graph showing head variance measured at upper port of the chamber according to the present invention.
Figure 12:
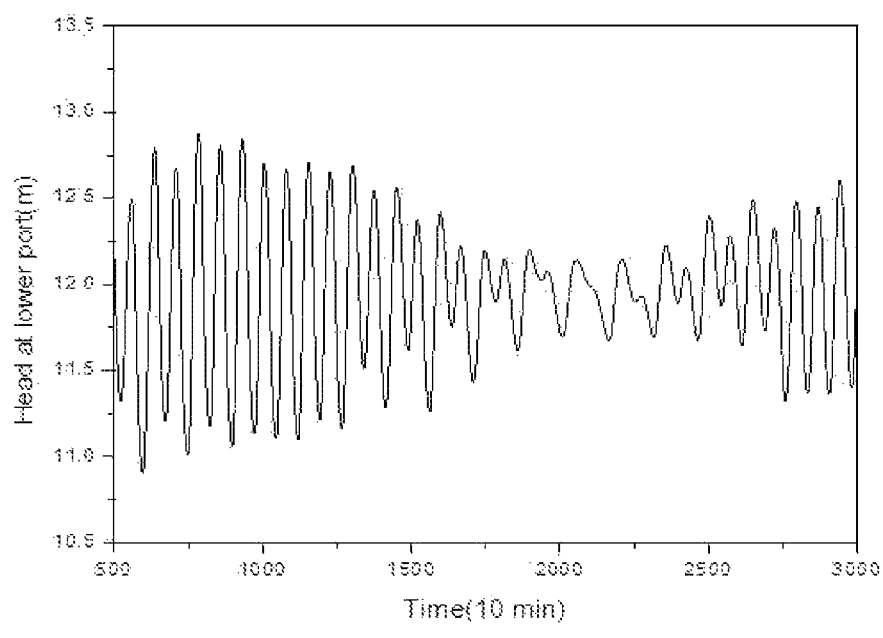
FIG. 12 is a graph showing head variance measured at lower port of the chamber according to the present invention.
Figure 13:
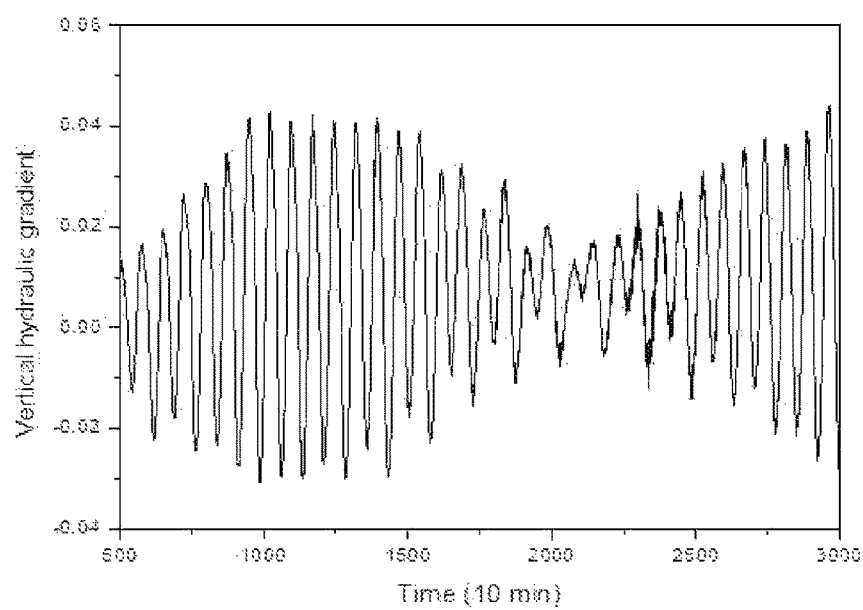
FIG. 13 is a graph showing vertical hydraulic gradient variance between upper and lower ports of the chamber by using difference in head between vertically distal two points of the chamber and the distance between upper and lower ports of the chamber.
Figure 14:
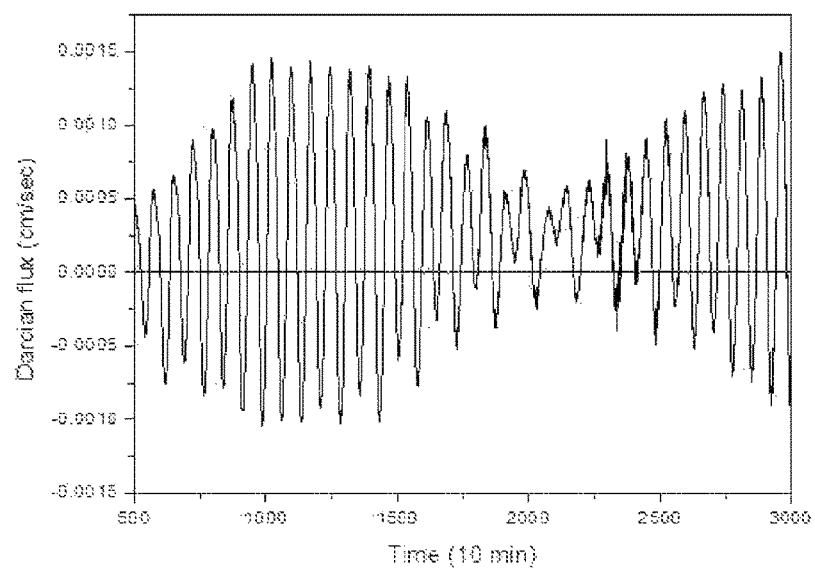
FIG. 14 is a graph showing Darcian flux variance at measurement location obtained by applying the vertical hydraulic conductivity (0.034 cm/sec) at the measurement location and the vertical hydraulic gradient to Darcy's law (Equation (1))
Figure 15:
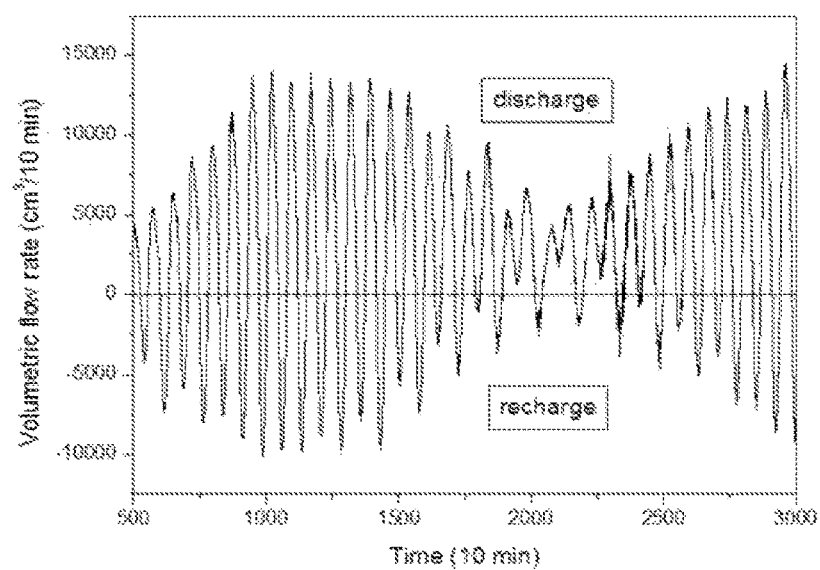
FIG. 15 is a graph showing the water exchange variance per time (10 minutes) at the measurement location obtained by multiplying Darcian flux at the measurement location and the cross-section area of the chamber 10 by elapsed time.

FIGS. 11 and 12 show the head variance measured at upper and lower ports of the chamber 10 according to the present invention. FIG. 13 shows the vertical hydraulic gradient variance calculated by subtracting the hydraulic head value at the upper port from the hydraulic head value at the lower port of the chamber 10, and dividing the hydraulic head difference between upper and lower ports of the chamber 10 by the vertical distance length (L) between the upper and lower ports. FIG. 14 shows Darcian flux (q) variance at measurement location obtained by multiplying the vertical hydraulic conductivity (K) at the measurement location by the vertical hydraulic gradient (i). FIG. 15 shows the water exchange variance at the surface water/sediment interface at the measurement location obtained by multiplying Darcian flux at the measurement location by the cross-section area of the chamber 10 and elapsed time.

The disadvantages, such as errors of values, caused by the existing measurement devices in which the locations where measurement tests are performed to measure the vertical hydraulic conductivity and the vertical hydraulic gradient are different can be removed to the utmost according to the water exchange meter of the present invention because the vertical hydraulic conductivity and the vertical hydraulic gradient are measured at the same place.

The hydraulic head measurement at two points of the chamber 10 uses the second automatic level measurers 55a and 55b which are commercialized, and the functions of the automatic level measurers 55a and 55b such as resolution of time measurements, measurement time period and so on can be maximized for use.

While the invention was described above with reference to the finite embodiments and drawings, the invention is not limited to the embodiments but can be modified and changed in various forms by those skilled in the art without departing from the technical concept of the invention and the equivalents of the appended claims.

What is claimed is:

1. A water exchange meter at surface water/sediment interface comprising:
    a chamber fixedly installed at the bottom of a stream and having a filling medium there inside;
    a measuring unit of vertical hydraulic conductivity including a storage pipe to communicate with the chamber by a connection line and to have a hydraulic head difference with the chamber for measuring the hydraulic head difference between upper and lower portions inside the chamber, and measuring the amount of the water induced into the storage pipe from the lower portion to the upper portion inside the chamber and measuring the flow rate of the water so as to obtain a saturated vertical hydraulic conductivity of the medium; and
    a vertical hydraulic gradient measuring unit installed around and at both sides of the chamber and is detachable from the chamber after the saturated vertical hydraulic conductivity is measured and the measuring unit of vertical hydraulic conductivity is removed from the chamber, and communicatedly connected to the chamber through upper and lower portions of the chamber for continuously measuring the vertical hydraulic gradient between two portions of the upper and lower of the chamber and by multiplying the vertical hydraulic gradient and the saturated vertical hydraulic conductivity so as to measure the water exchange through the chamber.

2. The water exchange meter at surface water/sediment interface according to claim 1, wherein the vertical hydraulic gradient measuring unit comprises:
    first and second pipes installed upright on the bottom of the stream and placed at both sides around the chamber to be respectively connected to the upper and lower portions of the chamber to communicate with each other; and second automatic level measurers respectively installed inside the bottom of the first and second pipes so as to measure hydraulic head variance.

3. The water exchange meter at surface water/sediment interface according to claim 1, wherein the connection line is characterized such that its one end is open and placed inside water when the storage pipe is removed and is placed apart from the surface water/sediment interface with a predetermined distance so that the sediment is not induced into the chamber.

* * * * *